United States Patent
Furner et al.

(10) Patent No.: US 6,780,382 B2
(45) Date of Patent: Aug. 24, 2004

(54) SIMMER PLATE DISPENSER FOR VOLATILE ACTIVE MATERIALS

(75) Inventors: Paul E. Furner, County of Racine, WI (US); Ralph G. Schwarz, County of Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 447 days.

(21) Appl. No.: 09/742,631

(22) Filed: Dec. 20, 2000

(65) Prior Publication Data

US 2001/0012495 A1 Aug. 9, 2001

Related U.S. Application Data

(63) Continuation-in-part of application No. 09/469,014, filed on Dec. 21, 1999, now abandoned.

(51) Int. Cl.$^7$ ................................................ A61L 9/03
(52) U.S. Cl. .................... 422/126; 431/291; 431/292
(58) Field of Search ................... 422/126, 305, 422/5; 44/275; 431/288, 291, 292, 294

(56) References Cited

U.S. PATENT DOCUMENTS

| | | |
|---|---|---|
| 2,254,906 A | 9/1941 | Petrulis |
| 2,713,256 A | 7/1955 | Oesterle et al. |
| 2,775,006 A | 12/1956 | Kranc |
| 3,910,753 A | 10/1975 | Lee |
| 4,013,397 A | 3/1977 | Neugart ........................ 431/291 |
| 4,427,366 A * | 1/1984 | Moore .......................... 431/291 |
| 4,755,135 A | 7/1988 | Kwok |
| 4,781,895 A | 11/1988 | Spector |
| 5,078,591 A | 1/1992 | Despres |
| 5,425,633 A | 6/1995 | Cole |
| 5,840,246 A * | 11/1998 | Hammons et al. .............. 422/4 |
| 5,955,034 A * | 9/1999 | Zaunbrecher et al. ........ 422/126 |

FOREIGN PATENT DOCUMENTS

| | | |
|---|---|---|
| EP | 1054054 A1 | 5/2000 |
| WO | WO89/06141 | 7/1989 |
| WO | WO 96 02794 | 2/1996 |

* cited by examiner

Primary Examiner—Elizabeth McKane (57) ABSTRACT

The present invention relates to dispensers for active materials, which dispensers employ heat conductive elements to distribute heat from a burning flame at a wick to a simmer plate and to the body of a solid fuel containing the active material, so as to more rapidly liquify the solid fuel, such as paraffin wax, and to more uniformly and intensely heat such fuels to volatilize the active material. The heat conductive elements and simmer plate are configured so as to engage said solid fuel, and to cause the flow of liquified fuel to the wick. The fuel may comprise various active ingredients, such as fragrances, air fresheners, deodorizers, odor eliminators, odor counteractants, insecticides, insect repellants, herbal and medicinal substances, disinfectants, sanitizers, mood enhancers, aroma therapy compositions, and the like, and may be provided in various forms.

9 Claims, 5 Drawing Sheets

FIG. 9 he present invention relates to means to provide a novel
SIMMER PLATE DISPENSER FOR VOLATILE ACTIVE MATERIALS

RELATED APPLICATION

This is a Continuation-in-Part application of Ser. No. 09/469,014, filed Dec. 21, 1999, now abandonded.

FEDERALLY SPONSORED RESEARCH OR DEVELOPMENT

Not Applicable.

BACKGROUND OF THE INVENTION

1. Technical Field

The present invention relates to means to provide a novel fuel burning apparatus, specifically a dispensing means, e.g. a dispensing device to disperse volatile active materials, including such compositions as fragrances, air fresheners, deodorizers, odor eliminators, odor counteractants, insecticides, insect repellants, herbals, medicinal substances, disinfectants, sanitizers, mood enhancers, aroma therapy compositions, and the like, into the atmosphere. More specifically, the present invention comprises a dispenser for more effective volatilization of active materials.

2. Background Art

Ordinary candles comprise a vertical, self-supporting body or column of wax, with a substantially horizontal top and a central longitudinal wick which extends through and above the wax. The exposed portion of the wick above the solid wax is lighted by a flame, and the heat generated by the lighted wick melts a small volume of the wax at the top of the candle, proximate the wick, establishing a puddle or reservoir of molten wax to serve as fuel for the flame on the wick. The capillary attraction of the molten wax and the wick, which is generally a structure of closely related fibers, causes the molten wax to travel through the wick to the flame, by which it is consumed. As the wax is consumed in this manner, the body of wax diminishes and the top surface thereof progressively lowers. The upper portion of the wick, extending above the lowering wax, is generally consumed by the flame.

Also well known are such candles or lights as tea lights, in which a body of paraffin is located in a container having a wick centrally disposed. At the lower end of the wick is a wick holder or wick clip, which functions to retain the wick in its perpendicular position, even as the paraffin is melted and liquified by the heat of the flame. In most such candles, the wick is a cotton material saturated with the paraffin, and burns with the paraffin, thus being consumable. In such candles, or lights or warmers employing the same, the visible flame diminishes as the wick is consumed, the container becomes hazardously over-heated by the flame, and the unit is time-limited by the volume of paraffin and size of the wick initially present. Further, after consumption of all of the wax in the unit, the container and the wick holder remain to be disposed of by the consumer.

Similarly, liquid fuel lamps are known in which a wick is supported with one end suspended in a reservoir of liquid fuel, such as lamp oil. By capillary action, the liquid fuel rises through the wick to the upper end thereof, where it is subjected to consumption by a flame. As fuel is consumed by the flame, additional fuel rises through the wick by capillary action to feed and maintain the flame. Permanent, or non-consumable, wicks are most frequently employed for this type of lamp.

It is also known to add active materials, such as fragrances, air fresheners, deodorizers, odor eliminators, odor counteractants, insecticides, insect repellants, herbal and medicinal substances, disinfectants, sanitizers, mood enhancers, aroma therapy compositions, and the like, directly to the fuel, whether a solid candle wax, a gel, or a liquid lamp fuel, to provide for dispensing of such compositions into the atmosphere upon consumption of the fuel at the flame, in the case of a liquid fuel or lamp oil, or by evaporation from the puddle of fuel formed by the melting of the wax or gel at the top of a candle. It is also known to provide such materials, hereinafter referred to as "actives," in a separate container which is heated by the flame, so as to cause their release to the atmosphere by evaporation, or to add such actives to a heated surface or to the surface of a melted pool of fuel to permit their evaporation, since release of actives by the flame of a lamp burning a liquid fuel is not highly efficient, due to consumption or breakdown of the active material in the flame. It is further known to employ wicks, which serve to bring the fuel to the flame, but are not themselves consumed by the flame.

In U.S. Pat. No. 2,254,906, Petrulis discloses a candle perfumer having a perfumed wick retained in an annular reservoir. The heat from the flame of a centrally located burning candle is conducted by thin wires which pass through the flame to an evaporator plate upon which the perfumed wick is located, to release the perfume from the wick.

Kranc, in U.S. Pat. No. 2,775,006, teaches a vaporizing unit that fits around and is heated by the flame of a central candle wick. The inner wall of the unit provides a vertical flue for the gases of the candle flame, and conducts heat to a volatile material contained therein, to evaporate a perfume, insecticide, medicament or the like.

U.S. Pat. No. 3,910,753, of Lee, discloses a wax burner comprising a vessel having a heat conducting metal heat sink surrounding and supporting a wick which projects upwardly, and has a heat conductive metal core means conducting heat into the heat sink, which acts as a wax melting surface. The wax burner may be fueled by paraffin wax or other suitable solid fuel, which may be added to the melting surface as required. The burner may constitute one or more burner units. In Lee, however, the fuel is neither supported or contained by the heat sink, which is configured much like a spool, with upper and lower flanges, or upper and lower flat, horizontal surfaces. The upper flange or upper surface acts as a melting rack, while the lower flange serves as a base for the heat sink, engaging the bottom surface of the burner vessel. Slots in the vertical surface of the heat sink provide means for the wax, melted by the heat sink, to flow from the exterior surface thereof to the internally located wick. Since the wick structure of the patent includes a metal core and a heat conductive metal sleeve about the wick, the wick structure is an integral portion of the heat sink of the burner assembly, and is non-consumable. This wick structure is indicated to require priming with wax prior to its first use. In use, solid wax is added to the melting rack, and replenished as necessary, or the entire vessel may be filled with wax. It is to be noted that the vessel itself is not used to conduct heat to the fuel, but only to contain it, and that a separate heat transfer system, i.e. the heat sink structure, which is independent of and distinct from the heat radiated by the flame itself, is utilized to achieve burning of the wax fuel. Even with this added heat transfer mechanism to assist in melting of the fuel, complete utilization of all of the fuel in the vessel is unlikely, even when the burner is permitted to burn to self-extinguishing, in view of the relative positioning of the lower flange and the wax conducting means of the heat sink (i.e. slots in the vertical surface thereof, above the lower flange).

In U.S. Pat. No. 2,713,256, Oesterle et al teach a votive candle having a wick extending downward in the bottom of the candle into a tapered central body projection, where said wick engages an adapter inserted into the cup for the votive. The adapter is provided with means to support the wick of the candle until the candle has completely burnt out, thereby leaving no wax or wick residue in the cup, enabling a new candle to be inserted into the cup without removal of the adapter. The adapter does not function to provide a more even or uniform burning of the candle, but to provide a proper positioning of the votive candle. When placed over the adapter, and the upwardly directed tube thereof, the flame on the wick comes into contact with a wicking material retained in the base of the tube, so as to ignite such wicking and assure that all of the melted wax is burned, thus leaving a clean cup containing no remains of the previous candle when a new candle is put in place. Moreover, the reference fails to disclose the dispensing of an active material to the atmosphere.

European Patent Application EP 1 054 054 A1, published Nov. 22, 2000, teaches a candle having a wick clip assembly for candles to be used on a supporting surface, wherein the wick clip provides enhanced control over heat transfer form the flame to the supporting surface upon which the candle rests. In this patent, the object of the wick clip assembly is to dissipate heat from the flame away from the support surface, essentially the opposite of the goal of the present invention. Moreover, the reference fails to disclose the dispensing of an active material to the atmosphere.

A number of additional patents teach the use of heat conductive elements to liquify solid fuel for consumption at a wick, or to dispense an element such as a fragrance or insect control material. These include U.S. Pat. No. 4,781,895 of Spector; U.S. Pat. No. 5,078,591 of Despres; U.S. Pat. No. 4,755,135 of Kwok; and U.S. Pat. No. 5,425,633 of Cole; as well as PCT Application WO 89/06141, assigned to Lamplight Farms, Inc.

None of the foregoing references, however, provide a long burning dispenser or dispensing device capable of rapidly and completely melting a solid fuel and ensuring efficient and complete utilization of the actives contained therein, while providing increased safety and convenient refilling. Further, the concept of the present invention offers highly decorative as well as functional dispensers and lamps, which may utilize a variety of gel and solid fuels, with the significant advantages of permitting rapid and convenient replacement of one active by another, and the ability to dispense actives having higher vaporization temperatures than the melting point of the carrier in which they are provided.

BRIEF SUMMARY OF THE INVENTION

As utilized herein, the term dispenser shall encompass the combination of a fuel containing a volatile active ingredient, and the means for heating said fuel so as to volatilize the active ingredient. On the other hand, the terms dispensing means, dispensing device, or dispensing apparatus shall be understood to refer only to the means for heating the fuel so as to achieve volatilization of the actives contained in the fuel. Thus, a dispenser is understood to comprise a fuel element and a dispensing apparatus, while a dispensing device is not inclusive of a fuel element. Accordingly, the manufacturer may provide dispensing devices and fuel elements independently or separately, and the consumer may join the two to form a dispenser of active materials.

The present invention provides a means for the dispensing of active materials, wherein said dispensing means ensures the maximum utilization of the active ingredient, which ingredient is encompassed within the fuel provided for a flame burning in said dispensing means. The dispensing devices of the present invention comprise a container for gel or solid fuels, and a wick, and provide an improved transfer of heat from a heat source, a flame burning the fuel at the wick, to the remaining fuel and to the container for said fuel. Such devices are preferably both functional and designed so as to be decorative or esthetically pleasing.

The dispenser of the present invention comprises a fuel element, a container for the fuel, which container comprises a heat conductive heat plate, or simmer plate, in direct contact, and in supporting or containing relationship, with the fuel element. The dispenser of the present invention may further comprise heat conductive elements to transfer heat by conductive means to the fuel and to the simmer plate, in addition to that heat transfer obtained by radiation from the flame. Such conductive elements result in improved transfer of heat from the burning wick to both the fuel and the heat plate with which the fuel is in contact, thereby heating the fuel over a relatively large surface. This, in turn, provides for rapid melting of solid and gel fuels, and rapid heating of the thus melted fuels, to provide a more uniformly heated pool of fuel, and to ensure a more complete volatilization of actives contained within the fuel. Since a goal of the present invention is to more rapidly heat the actives-containing fuel to temperatures which are not readily achieved by a conventional candle or lamp, so as to improve volatilization of the actives, the heat plate element shall hereinafter be referred to as a simmer plate.

The simmer plate, which acts both as a fuel container and a heat transfer means to heat the fuel, is shaped so as to collect the melted or liquified fuel at its lowest point, at which point a wick is located, so as to ensure that all fuel is fed to the wick, whereby the maximum consumption of the fuel is achieved. Thus, the simmer plate is preferably shaped as a bowl, or in the form of a funnel, with the lowest portion thereof preferably, but not necessarily centered. The wick is located so as to be at the lowest portion of the simmer plate, and may be positioned in a complementary depression in the fuel container or simmer plate The entire interior surface of the fuel container is preferably highly heat conductive, and supports, contains, and heats the fuel, although containers in which only a small portion of the interior surface acts as a simmer plate are within the scope of the present invention. The heat conductive surfaces of such containers shall be referred to as the simmer plate, and devices employing such simmer plates to dispense active materials shall be referred to, collectively, as simmer plate dispensing devices. In the preferred embodiments, the simmer plate shall comprise the entire fuel container.

Moreover, the simmer plate helps to control the shape and depth of the pool of fuel which is burned at the wick, and to maintain the constancy thereof. It is to be understood that the fuel utilized in the present invention may be initially in solid or gel form, but must be in liquid form for moving up the wick by capillary action to the flame, where it is consumed. Thus, the fuel used with the simmer plate dispensing device shall be such that it will not be transported by capillary action at ambient or room temperature, but requires heating to a liquified state, i.e. melting, to be subject to wicking action. For convenience, the term solid fuel shall be used hereinafter to refer to fuel in either a gel or conventional solid state, such as conventional candle wax. It is also to be understood that the fuel includes an active material to be dispensed, possibly in the flame at the burning wick, but preferably by evaporation from a liquid pool of fuel, which pool is formed by melting of the solid fuel, said liquid pool being heated by conductive heat transfer by the simmer plate, the wick, and heat exchange elements, as well as by radiant heat from the flame on the wick. By the use of the simmer plate technology of the present invention, in addition to conventional radiant heating of the surface of the fuel, the size and temperature of the liquid pool of fuel are better regulated, and as a result of greater heat transfer to the fuel, a melted, liquid pool thereof is more rapidly formed and heated to a relatively high temperature, and evaporation of actives contained therein is improved. Because the speed of achieving a pool of melted solid fuel is increased, faster and more intense fragrancing or other dispersion of active ingredients results, as well as a more complete usage of available active ingredient. In preferred embodiments of the present invention, a pool of liquid, i.e. melted, fuel rests upon the surface of the heat conductive simmer plate. This pool of fuel may contain unmelted fuel in the solid state, as well as melted fuel.

Generally, the simmer plate dispensing device embodies both a simmer plate and a heat conductive element, which element is in close proximity to the flame, to ensure more uniform and rapid heat distribution from the flame upon the wick. The wick is affixed in its preferred position by means of crimping to a wick clip, press fit, or by other appropriate conventional means, such as by welding, soldering, or cementing, as with an adhesive. The wick may be any filamentary body which is sufficiently sturdy, which will burn with a steady flame, and which is capable of drawing up the molten candle fuel by capillary action. Such a wick may be of any conventional consumable wick material, such as cotton, cellulose, nylon, or paper. The wick may preferably be located in the center of the candle, or may be off-center as desired. The presence of two or more wicks is also within the scope of the present invention.

The heat conductive element may constitute a portion of the simmer plate itself, formed or bent to be in proximity to the flame, or may be a separate assembly which is utilized in conjunction with the simmer plate and consumable wick. For example, the simmer plate may constitute a bowl shaped container having its outer periphery in close proximity to the flame, such as a container in which the upper lip of the bowl is formed so as to curve back toward the center of the bowl. Alternatively, the simmer plate may have one or more raised portions, or lobes, which may act not only to absorb and distribute heat by conduction, but to channel or direct the flow of liquid fuel to the wick, and/or to engage the fuel element in such a manner as to properly position it. Further, the lobes may constitute areas of higher heat conductivity than surrounding areas of the container.

However, as indicated, the heat conductive element may also be a separate and independent assembly, including means to support and locate the wick, which assembly may be replaced as necessary or desired, but is preferably a permanent feature of the simmer plate. The heat conductive element assembly may take the form of heat fins or heat conductive surfaces having either vertical or horizontal orientation, or elements of both. In preferred embodiments, such heat conductive elements are heated by contact with the flame, or by radiation of heat from the flame, and conduct such heat to the simmer plate and to the fuel so as to more efficiently heat the fuel.

It is to be understood that the heat conductive elements may be so situated and shaped as to engage or interlock with a replaceable or refillable solid fuel element, such as being of a specific shape or configuration that will engage or mate with a complementarily shaped fuel element. In a similar fashion, the heat conductive elements and/or the fuel container may be formed in such a manner as to permit placement of fuel elements of specific configuration, such as balls, cylinders, or cubes, for example, in a preferred position in proximity to the heat conductive elements themselves, or to the wick, in such a manner as to maximize heat transfer to said fuel elements.

The present invention is thus a dispenser of actives, said dispenser comprising, in its most basic form, a container, and a solid fuel element having a consumable wick and containing a volatile active material, wherein said container is configured so as to cause the flow of liquid fuel to the wick, at which wick the fuel may be burned to produce heat so as to liquify said solid fuel element. In a preferred embodiment, the simmer plate dispenser constitutes a container comprising a simmer plate configured so as to cause the flow of liquid fuel to the wick, a consumable wick, and a heat conductive element to conduct heat from a flame at the wick to the simmer plate, which is in contact with a solid fuel element containing a volatile active material. In such a preferred embodiment, the fuel is a solid wax, which is melted by heat conducted via the heat conductive element and the simmer plate, to provide liquid fuel to the flame via the wick. The solid wax fuel comprises an active ingredient, such as a fragrance or insect control agent, which may be released to the atmosphere either by consumption with the fuel at the flame, or preferably by evaporation from the melted solid fuel, or by both mechanisms.

In one aspect, the invention provides a method for fueling a long-burning actives dispersing simmer plate device, wherein replenishment fuel is added as necessary or desired, without the need to extinguish the flame while additional fuel is provided. By use of a conductive simmer plate, the solid fuel is heated over a relatively large surface area, to speed the melting and heating of a large volume of solid wax or fuel. The liquid pool of wax or fuel thus formed acts both as a reservoir and a safety feature, since such a pool will act to extinguish a flame at the wick if the pool level becomes excessive, or if the device is tilted excessively, particularly as the simmer plate is so configured as to cause liquid fuel to flow to the wick.

The objects of the present invention therefore include providing dispensers of active materials, which dispensers are:

(a) capable of burning for extended periods without close attention;

(b) capable of burning a variety of fuels which may be conveniently and rapidly changed or added as desired;

(c) able to more rapidly and intensely dispense actives such as fragrances;

(d) able to dispense insect control agents having vaporization temperatures higher than the melting point of the wax in which they are incorporated;

(e) capable of dispensing a variety of actives which may be conveniently and rapidly changed or added as desired;

(f) able to produce a pool of melted wax having a high surface area for greater volatilization of active material;

(g) highly decorative;

(h) self cleansing, in the sense that they leave little or no residue of unburned fuels; and (i) relatively inexpensive to produce, and economical for the consumer.

The use of the simmer plate technology of the present invention may also provide such advantages as elimination of tunneling, significant reduction of retention of wax at the conclusion of the burn, elimination of walking or off-center wicks, while also giving a large pool of liquid wax with a relatively small flame in a relatively short time period, thus providing more rapid and intense dispersion of the active material. In addition, the container may be of almost any shape desired, providing for great aesthetic possibilities. Since the fuel element, containing the active ingredient, is provided as a separate unit, the consumer may be provided a great number of choices as to the active ingredient to be dispensed, and the configuration of the fuel element may be varied to provide a large choice of shapes, such as seasonably decorative items. In addition, the fuel element may be so configured as to cooperatively engage the simmer plate and/or the heat conductive element, in such a manner as to provide the consumer the greatest degree of ease in placement of the fuel element in optimal position in the simmer plate dispenser, with the least possibility of incorrect placement.

Thus, an object of the present invention is to provide a dispenser for a volatile active material, said dispenser comprising, in combination, a fuel element comprising a solid fuel containing said active material, a container for said fuel element, and, a wick at which fuel may be burned to produce heat so as to melt said solid fuel, wherein said container is configured so as to cause the flow of melted fuel to said wick.

Accordingly, it is an object of the present invention to provide a dispenser for dispersion of a volatile active material selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof, wherein said active is incorporated in a fuel element comprising a fuel selected from the group consisting of paraffin, beeswax, montan wax, carnauba wax, microcrystalline wax, stearic acid, fatty alcohols, fatty acids, fatty esters, and gels incorporating such fuels, in a form selected from the group consisting of pucks, donuts, chips, slivers, balls, pellets, shavings, particulates, cubes, discs, three dimensional shapes, and wafers, or in any other suitable shape, wherein said container is a concave simmer plate further comprising a heat conductive element chosen from the group consisting of lobes, fins, wick holders, and combinations thereof, and said heat conductive element cooperatively engages said fuel element.

Similarly, a further object of the present invention is to provide a simmer plate dispenser for active materials, said dispenser comprising, in combination, a meltable solid fuel comprising a volatile active material, a consumable wick, a heat conductive base upon which said fuel rests, and heat conductive elements by which heat is conducted to said base from a flame upon said wick, whereby a pool of heated liquid fuel is created from which said active material volatilizes, wherein said heat conductive base is configured so as to cause the flow of said heated liquid fuel to said wick for combustion, said base and said elements are configured so as to cooperatively engage said fuel, and said active material is selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof.

Accordingly, an object of the present invention includes a simmer plate dispenser for dispersing an active ingredient selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof, said active ingredient being incorporated in a solid or gel fuel, which fuel is melted by a heat conductive element selected from lobes, fins, wick holders, or combinations thereof, the heat conductive element being heated by a flame at a wick, a heat conductive base upon which the fuel rests, the base being configured so as to cause the flow of melted fuel to the wick, and the heat conductive element configured to cooperatively engage the fuel element.

A further object is to provide a simmer plate dispenser for dispersing an active ingredient selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof, said dispenser comprising a replaceable fuel containing said ingredient, and a dispensing device comprising a heat conductive simmer plate, a wick, and a heat conductive element to collect heat from a flame at said wick and conduct said heat to said simmer plate to thereby melt said fuel containing said active ingredient and form a pool of liquid fuel on the surface of said simmer plate, wherein said dispensing device is configured to position and engage said fuel on said simmer plate for rapid melting, said simmer plate is shaped so as to cause said pool of liquid fuel to flow to said wick, and said active ingredient is selected so as to evaporate from said pool of liquid fuel.

Also desired is a solid replacement element for a dispenser of volatile active materials, said element comprising a solid fuel having a consumable wick element, and a volatile active ingredient selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof.

Applicants further teach a dispensing device for dispersing a volatile active material, said device comprising a heat conductive container having affixed thereto a wick, said container configured so as to cause the flow of liquid contents to the wick and to engage and melt a solid fuel element containing said volatile active material.

These and still other objects and advantages of the present invention will be apparent from the description which follows. The following description is merely of the preferred embodiments, and the claims should be looked to in order to understand the full scope of the invention.

DETAILED DESCRIPTION OF THE INVENTION

Figure 1:
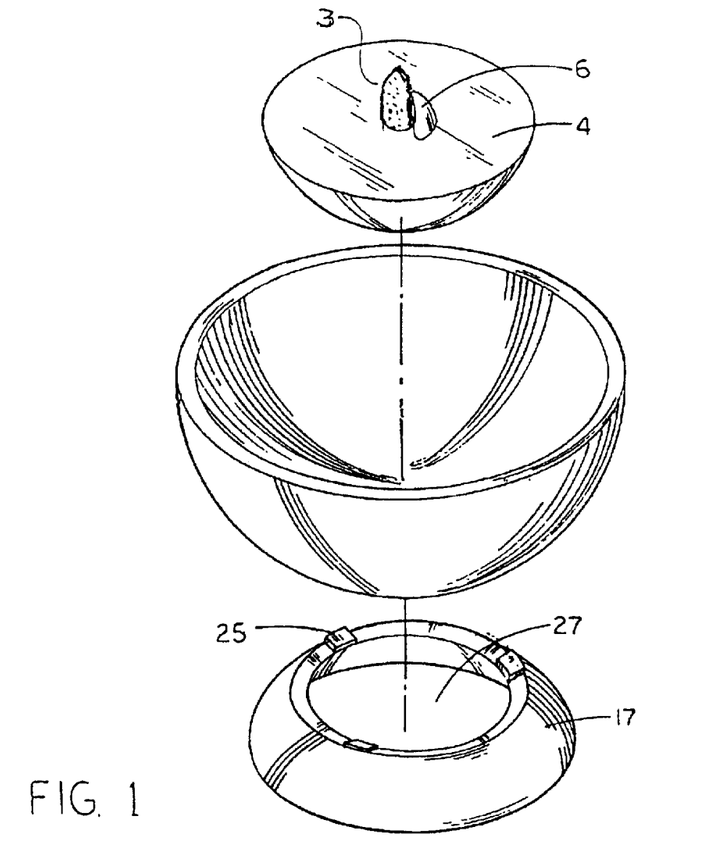
FIG. 1 illustrates the basic concept of the simmer plate dispenser, in simplified perspective view.
Figure 2:
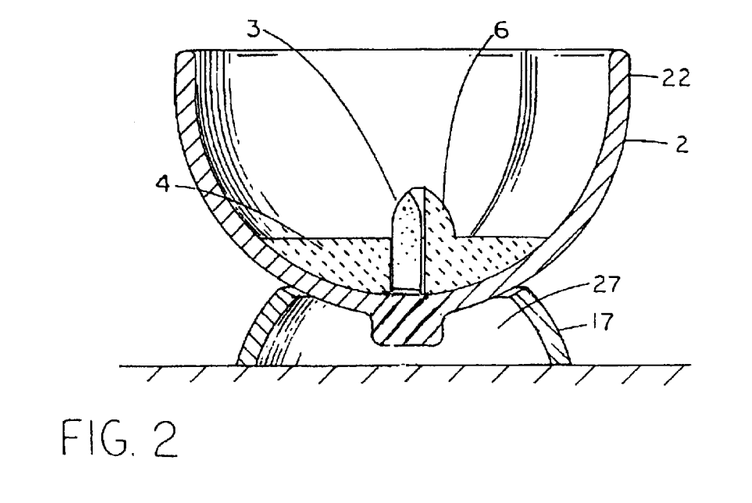
FIG. 2 illustrates a basic simmer plate dispenser of the present invention, in simplified cross section.

FIGS. 1 and 2 illustrate the concept of the simmer plate dispenser in its most basic form. As illustrated, a heat conductive bowl shaped simmer plate, 2, is provided, which transfers heat from the heat source, a flame (not shown) located on wick 3, by means of heat conduction, to a solid fuel element, 4, which rests upon the surface of the simmer plate. For purposes of illustration, and for clarity, but intending no limitation, the wick is illustrated as being of a relatively large diameter, rather than as a conventional fibrous consumable wick of small diameter. It is to be understood that the wick is conventionally positioned and attached to and within the solid fuel element, 4, such as with a wick clip (not shown). The simmer plate, 2, is heated directly by the flame on the wick, 3, either by direct contact therewith, or by radiation, as in FIGS. 1 and 2, as a result of the simmer plate being shaped so as to have a portion in proximity to the flame, the diameter of the simmer plate bowl being such as to permit the inner surfaces thereof to absorb appreciable amounts of heat from the flame.

Figure 4:
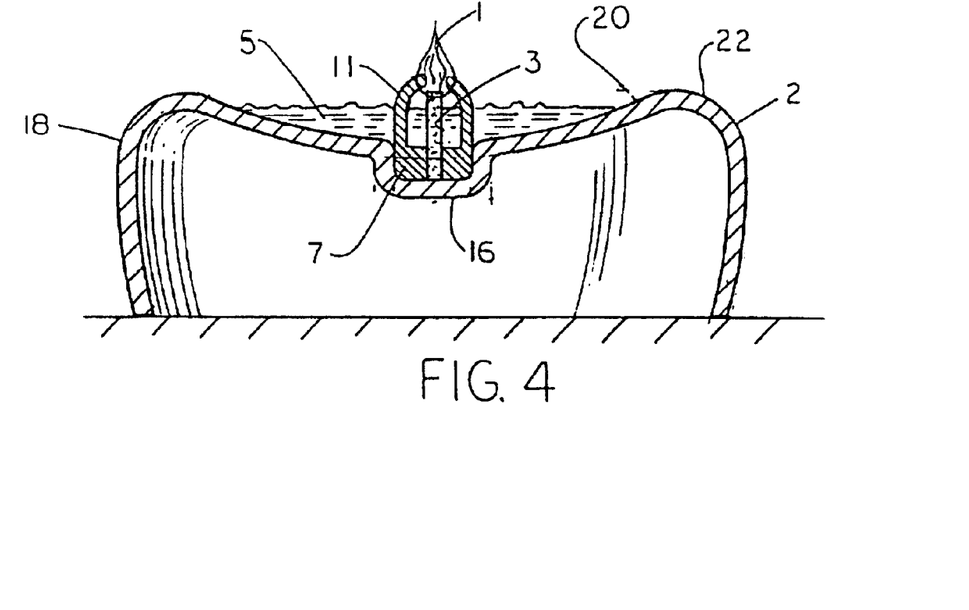
FIGS. 4, and 5 are cross sectional representations of simmer plate dispensers employing simmer plates of differing configuration.

In a simmer plate dispensing apparatus, the wick may be held by a conventional wick clip, or may be held in place by a heat conductive element, such as a wick holder, as shown in FIG. 4, or affixed to or retained by the fuel element by other appropriate means. To assure efficient heat exchange between the flame at the wick and the simmer plate, the simmer plate of FIGS. 1 and 2 is shaped so as to have a portion, in this case a raised shoulder, 22, of the simmer plate, which is in proximity to, and heated by, the flame of the burning wick, which results in heat being transferred rapidly to the fuel by both conduction through the simmer plate and by radiation from the flame. The melted fuel, and the active material incorporated therein, are in contact with the air for evaporation of the active, while the solid fuel element is subject to melting from heat from the flame and the simmer plate. As opposed to a conventional candle, transfer of heat from the flame to the fuel with a simmer plate device is primarily by conduction, either through the simmer plate or through additional heat conductive means, rather than by radiation, and is thus considerably more efficient, resulting in more rapid and more uniform melting of solid fuel and formation of a pool of liquid fuel, a more efficient burn, and easier lighting. However, difficulty in lighting the wick may be encountered. For this reason, a starter bump, 6, of fuel, is provided in close proximity to the surface of the wick. As illustrated, this bump is most easily molded directly into the shape of the fuel element, and provides a ready source of liquid fuel to the wick when a match or other appropriate source of flame is employed to start the wick burning, which source of flame will melt the starting bump.

The simmer plate of FIGS. 1 and 2 is shaped so as to have a raised outer shoulder, 22, thereby containing the resultant pool of melted fuel. It is to be understood that the simmer plate may be in the form of a tray, bowl, concave plate, or other configuration which is capable of holding a pool of hot liquid fuel, and is so shaped as to funnel or channel the liquified, i.e. melted, fuel to the wick. The bowl shape of FIGS. 1 and 2 is a preferred embodiment. The entire dispensing device may constitute a container in itself, as shown, or may also be surrounded by a separate container, as illustrated in FIGS. 5 through 9, hereinafter. In the embodiment shown in FIGS. 1 and 2, the simmer plate rests upon a non-conductive base, 17, or legs of non-conductive or insulating material, so as to permit placement upon a table, counter, or other surface. The non-conductive base, as illustrated, comprises contact points, 25, so as to minimize the amount of contact between the base and the simmer plate, and to create an insulating air gap, 27, between the simmer plate and the surface upon which the assembly rests.

Figure 5:
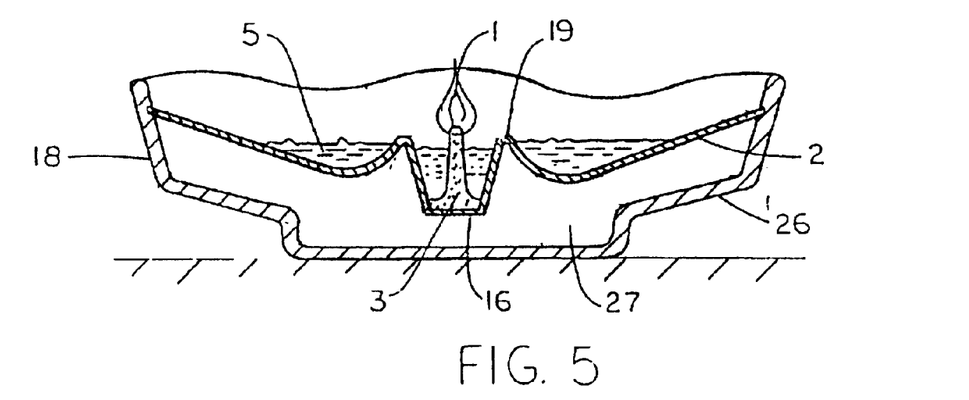

The simmer plate may be of any heat conductive material, such as brass, aluminum, steel, copper, stainless steel, silver, tin, bronze, zinc, iron, clad materials, heat conductive polymers, ceramics, glass, or any other suitable heat conductive material or combination of such materials. As shown in FIG. 2, the fuel is preferably located in direct contact with the surface of the simmer plate, 2, which plate may, if desired, be constructed so as to have a non-conductive lower surface, so that the simmer plate may rest upon a table surface or such. Such a configuration may result from a clad material, a conductive material coated with a non-conductive material, a non-conductive material having an insert of a heat conductive material, or other suitable arrangements to permit the simmer plate to be cool enough on the bottom surface to permit ease of handling, and/or placement upon surfaces not suitable for contact with heated bodies, as will be discussed hereinafter, and as shown in FIG. 5, for example.

The wick, 3, preferably constitutes a conventional wicking material, such as such as cotton, cellulose, nylon, or paper, or a porous ceramic, fiber glass, or pumice wick, or the like, which by capillary action will carry liquid fuel to the flame. Suitable permanent or non-consumable wicks may comprise such materials as porous ceramics; porous metals; fiber glass; metal fiber; compressed sand, glass, metal, or ceramic microspheres; foamed or porous glass, either natural or man-made, such as pumice or perlite; gypsum; and chalk. In addition, non-combustible materials such as metal may be used to create capillary grooves, spaces, or tubes in or between closely spaced sheets. However, for purposes of the present invention, the use of conventional consumable wicks is preferred. The wick, 3, may be located in the center of the simmer plate, 2, or may be off-center as desired, provided that the simmer plate is configured so as to channel or funnel the melted fuel to said wick. The presence of two or more wicks is also within the scope of the present invention, as is the use of wicks which are provided as part of the simmer plate assembly, a wick holding heat fin assembly, or as part of a removable separate heat clip or wick holder. When provided as an element of the simmer plate, the wick may be attached to, adhered to, or incorporated in any manner which does not inhibit the capillary action of the wick in feeding liquid fuel to the flame.

The fuel may be a solid fuel which is liquified, i.e. melted, before or during consumption, such as any conventional candle wax, such as petrolatum or a microwax, including paraffin, beeswax, montan wax, carnauba wax, microcrystalline wax, stearic acid, fatty alcohols, fatty acids, fatty esters, or the like, or gels incorporating such fuels, having melting temperatures above ambient, but below the flame temperature of a wick burning such fuel. Such solid fuel may be colored for decorative effect, if so desired, and may be shaped to fit any given configuration of simmer plate. For example, the bottom of a solid fuel element should be curved complementarily to the shape of the simmer plate upon which it is to rest. Further, the solid fuel may take the form of wax pucks, donuts, chips, slivers, balls, pellets, shavings, particulates, cubes, discs, three dimensional shapes, and wafers, or the like, in sizes suitable for ease of addition to the simmer plate or fuel pool. The solid fuel element further contains actives, as defined hereinabove, such as fragrances, herbals, disinfectants, air purifiers, insecticides, or insect repellents, to be evaporated from the fuel pool as a result of the temperature of said pool being elevated above the melting temperature of the solid fuel by the simmer plate and heat conductive elements.

An important aspect of the present invention is the additional use of a heat conductive element in conjunction with the simmer plate, or as part of the simmer plate. In addition to taking the form of a heat conductive lobe in or on the surface of the simmer plate, the heat conductive element may take the form of a portion of a heat conductive wick holder which aids in positioning of the wick, or may be present merely as a heat fin, to aid in heat distribution by the conduction of heat from the flame to the fuel. Such heat conductive elements may take a variety of shapes, as exemplified by FIGS. 3a through 3g, which illustrate various suitable heat conductive elements, but clearly do not illustrate all possible configurations. The heat conductive element may support or hold the wick, as in FIGS. 3b, 3e, 3f, and 3g, or may merely pass through the flame or be concentric thereabout without contacting the wick, as in FIGS. 3a, 3c, and 3d, so as to collect the greatest amount of heat possible from the flame. Shown in conjunction with a wick, the heat conductive element is designed to be in close proximity to, or in direct contact with, a flame upon said wick, so as to provide a heat collection and distribution member. In these drawings, the wick, 3, is in heat exchange proximity to various forms of heat conductive elements or fins, which act as heat distribution means. The distance of the heat conductive element from the flame should be controlled so as to achieve a suitable degree of heat exchange, i.e. the heat fin should be less distant from the flame than that distance at which radiant heat from the flame would exceed the amount of heat collected and conducted by the heat fin to the fuel or the simmer plate. Due to the variable heat conductivity of materials suitable for use in heat conductive elements, it is not feasible to designate a specific distance between the flame and the heat conductive element or fin, but it is clear that the greatest conductive heat transfer to the fuel and the simmer plate occurs when a highly conductive heat fin passes directly through the hottest portion of the flame, and that the amount of heat transferred to a heat conductive element or heat fin decreases as the distance from the flame increases. The heat collected from the flame by the heat conductive element, or heat fin, is transferred directly, by conduction, to fuel which is in contact with the heat fin, to the simmer plate, and thence to fuel which is in contact with the simmer plate. The rate of heat flow by conduction greatly exceeds the rate of heat transfer resulting from the radiant heat generated at the flame, resulting in a more efficient use thereof. Thus, the fuel element is melted more rapidly, and the melted fuel is heated to a greater extent, than it would be absent the heat conductive elements.

Figure 3A:
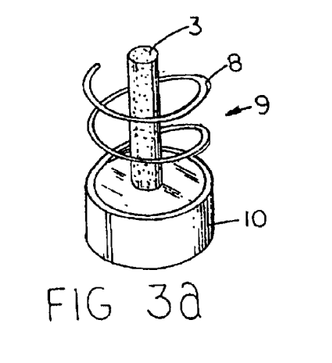
FIGS. 3a through 3e are perspective views of various exemplary heat conductive elements in the form of wick holders, and fins, which are suitable for use in this invention.

In FIG. 3a, a helical wire, 8, surrounds the wick, (again, not drawn to scale) 3, and the flame (not shown) which rises therefrom during consumption of the fuel. The helical wire which, with its heat conductive mounting means, 10, comprises a form of heat fin assembly, 9, may be directly encompassed by a solid fuel element, or mounted upon or into a simmer plate, in such a manner that conductive heat transfer loss is minimized. The helical wire is in close proximity to the wick and thus the flame, but may also pass directly through the flame for greater heat transfer. The heat which is collected by the helical wire passes directly, by conduction, to the simmer plate 2, via mounting means 10, and to any fuel which is in contact with the helical wire fin.

Figure 3B:
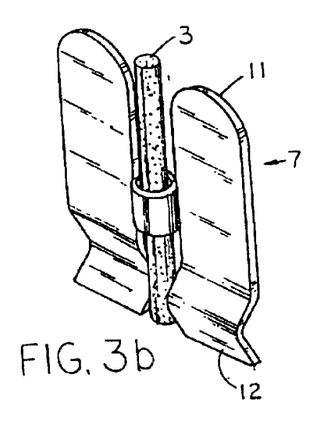

FIG. 3b illustrates a heat conductive wick holder, 7, in which a wick, 3, is held by mounting means, 10, to project a short distance above the wings or fins, 11, of the holder. The fins, 11, preferably are fashioned of a highly heat conductive metal. The conductive wick holder, 7, comprising the wick mounting means, 10, and the fins, 11, may provide positioning means, 12, designed to engage corresponding recesses or positioning elements within the solid fuel element, or in the simmer plate (not shown).

Figure 3C:
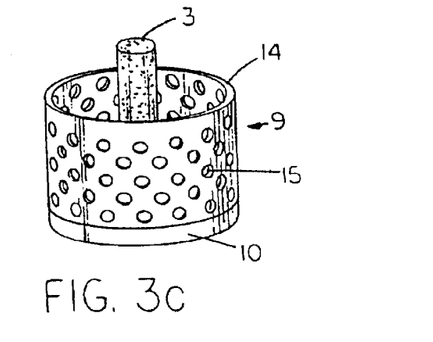

Similarly, FIG. 3c illustrates a heat fin assembly, 9, comprising a circular heat fin, 14, surrounding the wick, 3, and having perforations, 15, or holes therein to permit flow of air and liquid fuel from the outermost side thereof to the innermost side thereof to fuel the burning of the fuel at the wick, 3. The metallic fin, 14, may also comprise a metal mesh, rather than a perforated metal foil as illustrated. This type of heat fin may also be directly attached to the simmer plate, or may incorporate a wick clip, 10, by means or which the heat fin may be incorporated within a solid fuel element. It may be seen that the heat fin is so positioned, surrounding the wick and in close proximity thereto, so as to receive heat by radiation from the flame on the wick, which heat is then transmitted by conduction to the simmer plate.

Figure 3D:
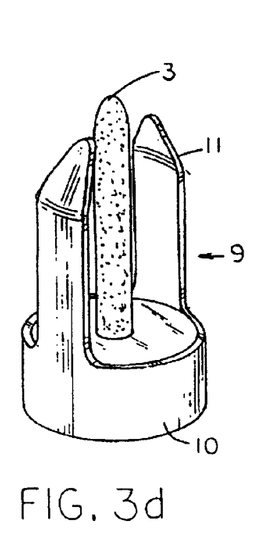

FIG. 3d illustrates a heat fin assembly, 9, having a clip mounting means, 10, suitable for inclusion in a solid fuel element, and having fins, 11, parallel to the wick itself. Such a heat fin assembly is particularly suitable for use in a simmer plate as shown in FIG. 4.

Figure 3E:
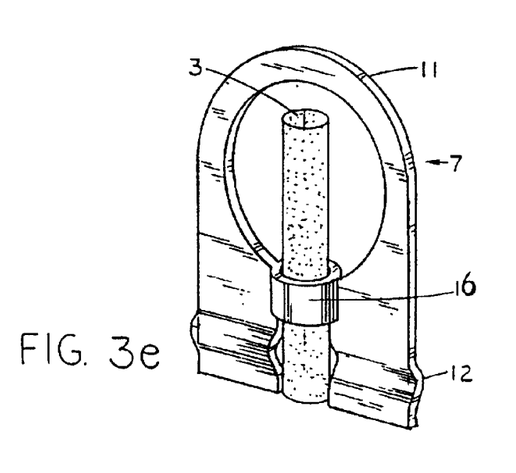

FIG. 3e shows a heat fin assembly comprising a wick holder, 7, and a single fin, 11, configured so as to pass through the flame above the wick, 3, in such a manner as to collect and distribute the maximum amount of heat available. In this configuration of wick holder, the wick is positioned by mounting means 28, e.g. a clamp or encircling ring, while the holder may be positioned in place in a solid fuel element during preparation thereof by means of means of positioning means 12, or other suitable means.

It is to be emphasized that the heat generated at the flame is conducted by means of heat conductive elements to both the simmer plate and to the solid fuel, causing it to liquify or melt, thus providing a pool of liquid fuel, 5, as shown in FIGS. 4 and 5, which is available to the wick to support further combustion. As illustrated in FIGS. 1 and 2, the solid fuel is located above and in direct contact with the simmer plate, which also serves to contain the solid fuel and the liquid fuel derived therefrom by the melting thereof. The direct contact of the simmer plate and the solid fuel improves heat flow to the fuel, ensuring a more rapid and complete melting thereof. As the fuel is consumed by the flame, additional melted fuel will be channeled or funneled to the wick as a result of the shape of the simmer plate being designed to accomplish such flow. Additional fuel elements may be introduced as desired or necessary, to replenish those which are consumed, or if desired, to change or modify the actives being dispersed. Further, as the simmer plate and heat conductive elements increase the temperature of the liquified fuel with which they are in contact, active materials in the fuel will be more rapidly volatilized and released to the atmosphere, thus providing for more efficient dispersal thereof.

One preferred embodiment of the use of a simmer plate for dispensing actives may be referred to as a simmer plate dispenser, 18, as illustrated, for example, in FIGS. 4 and 5. FIG. 4 shows a one piece construction, favorable for low cost production, which uses a wick holder, 7, having fins 11, and in which the entire remaining assembly may be considered to constitute a simmer plate. As shown, the simmer plate, 2, is shaped so as to provide a bowl shaped container, 20, having a central depression, 16, for placement of a fuel element incorporating a heat conductive wick holder, 7. In a simmer plate dispenser produced in this form, the wick holder, 7, functioned both to position the wick, 3, and to transmit heat, via fins 11, from the flame, 1, to the fuel as well as to the simmer plate, 2, which constituted the container for the pool of fuel, 5, a pool of melted wax. For this illustration, the solid fuel element is not shown, but the fuel is shown as having been completely melted, at which point the wick is supported in position by the wick holder, 7. The wax pool was formed by the melting of a solid fuel element, such as fragranced paraffin, which was placed in the bowl shaped container, 20, and melted by heat conducted from the flame by the fins to the simmer plate, 2. The height of the raised shoulder, 22, of the bowl shaped container was chosen so as to provide a pool of adequate depth to contain a sufficient supply of fuel to burn for a desired period of time. By use of a highly heat conductive metal, such as aluminum or copper, for the simmer plate, and proper dimensioning of the unit, the entire mass of the solid fuel element added to the bowl was rapidly melted from the bottom, resulting in a pool of fuel, 5, which filled the bowl sufficiently to ensure a lengthy burn time. As the level of the pool dropped, additional wax, in the form of chips, shavings, granules, cubes, or small balls, was added, and rapidly melted. It is to be noted that while the simmer plate dispenser, 18, illustrated by FIG. 4 was essentially circular, the shape is not critical, and may be varied, such as in the form of a square, triangle, oval, rectangle, clover, diamond, etc, provided that it is shaped so as to channel the liquid fuel to the wick. It is also possible to locate the wick, 3, in an off-center location, for esthetic effect or for increased efficiency, dependent upon the shape and dimensions chosen for the simmer plate, or to employ a plurality of wicks located at various positions within the bowl. Raised portions, or lobes, may be present to define separate zones within such various shapes, and/or to facilitate heat conduction. For example, a clover shaped simmer plate may be produced, having separate wicks and fuel elements containing a different active material in each of the leaves of the clover, with raised portions separating the zones, and each such zone configured to channel the liquified fuel to the wick located therein. Such a simmer plate offers the opportunity for the consumer to choose among varying actives, or to mix actives by burning one, two, three, or more wicks at any given time.

A second example of a simmer plate dispenser, 18, is shown in FIG. 5, wherein a two piece construction is illustrated, also having a pool of fuel, 5, constituted of melted wax. In this design, the wick, 3, is proximate a heat lobe, 19, a raised portion of the simmer plate, 2. The heat conductive element, or lobe, conducts heat to the rest of the simmer plate, which is so shaped as to engage and/or partially rest upon the sides or slope of a non-conductive container, 26. The container may be made of any suitable material, such as glass, ceramic, plastic, wood, etc., and may be of any desired shape, the selection of such being determined, for example, by esthetics. The simmer plate is configured in such a manner as to leave an insulating air gap, 27, between the simmer plate and the container to limit heat transfer to the container, for safety, as well as to permit the greatest possible heat transfer from the simmer plate to the pool of fuel, 5. As with the one piece construction simmer plate of FIG. 4, the simmer plate may preferably be constructed of a stamped heat conductive metal. In this illustration, the wick, 3, is shown as being positioned within the central depression, 16, of the simmer plate, proximate the lobes or heat conductive elements, 19, of the simmer plate. The simmer plate and lobes may also be designed to conduct the heat from the flame in a non-concentric pattern, allowing shapes other than round. Thus, by use of heat conducting lobes, constituting raised areas of the simmer plate, simmer plates may be oval, triangular, rectangular, or any other desired shape.

Figure 6:
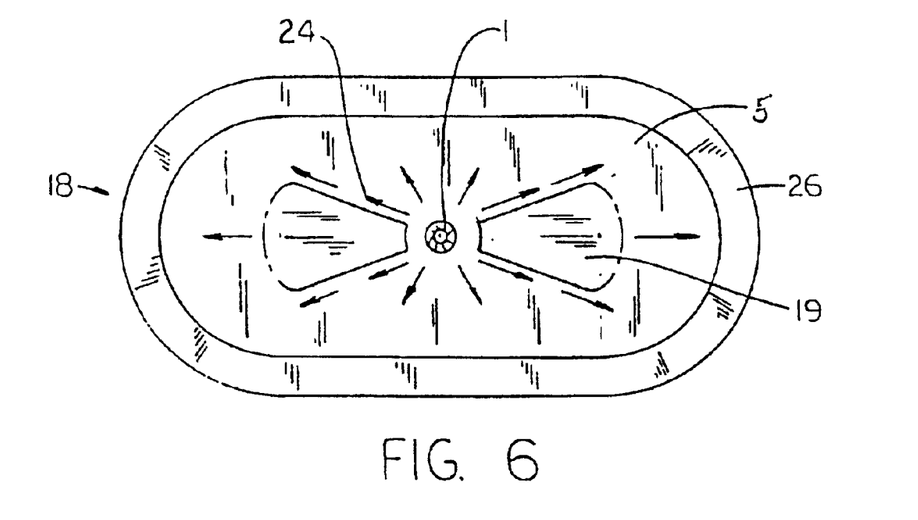
FIGS. 6 and 7 are a top view and a perspective view of an oval simmer plate dispenser employing heat lobes in the form of raised portions of the simmer plate.
Figure 7:
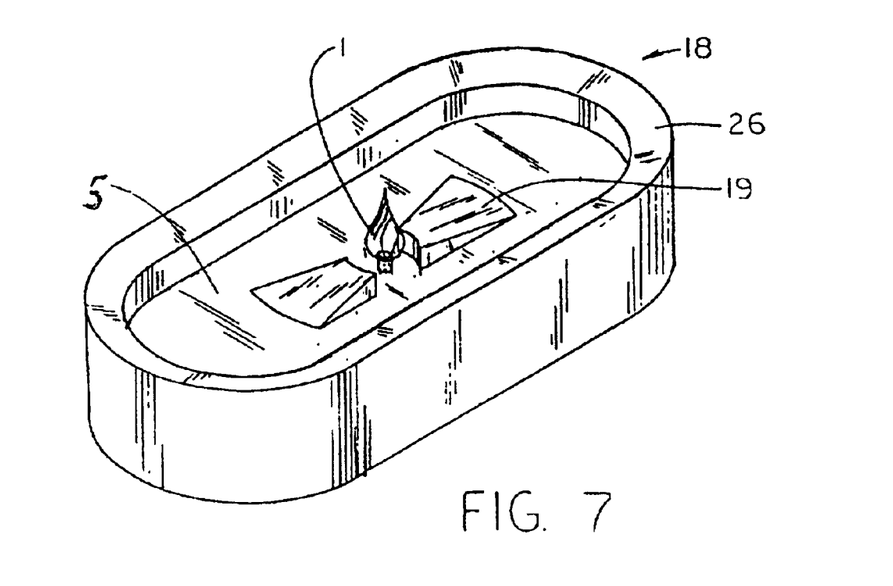

Exemplary of the various shapes which may be utilized is an oval heat plate dispenser, such as shown in FIGS. 6 and 7. Shown is a simmer plate dispenser, 18, comprising an oval non-conductive container, 26, in which is located a simmer plate, not shown, but present under the pool of liquified fuel, 5, said simmer plate having raised lobes 19, in close proximity to a flame 1, centrally located. Arrows, 24, indicate the direction of conductive heat flow away from the flame via the simmer plate, to enhance the melting of fuel, and heating of the pool of fuel located upon the surface of the simmer plate. The simmer plate is so configured as to cause the flow of liquified or melted fuel to the base of the wick, whereby it is consumed in the flame.

Figure 8:
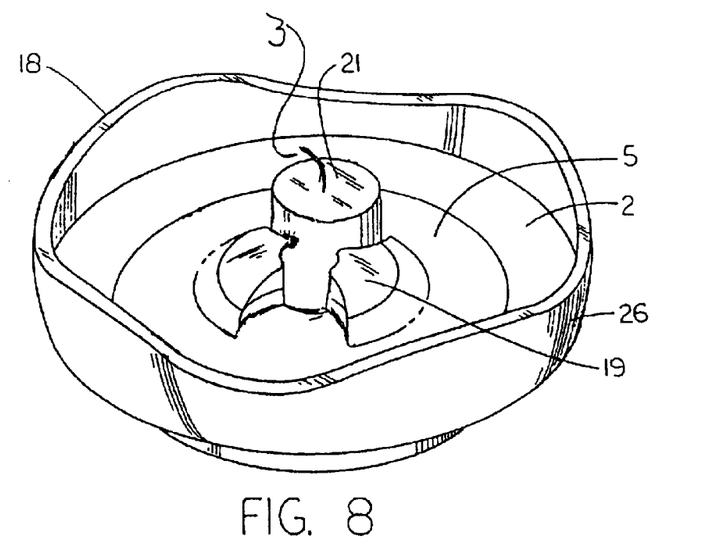
FIG. 8 illustrates a perspective view of a simmer plate dispenser employing a wick, and a refill fuel element in the form of an actives-containing ball positioned adjacent the wick by heat lobes formed as part of the simmer plate.
Figure 9:
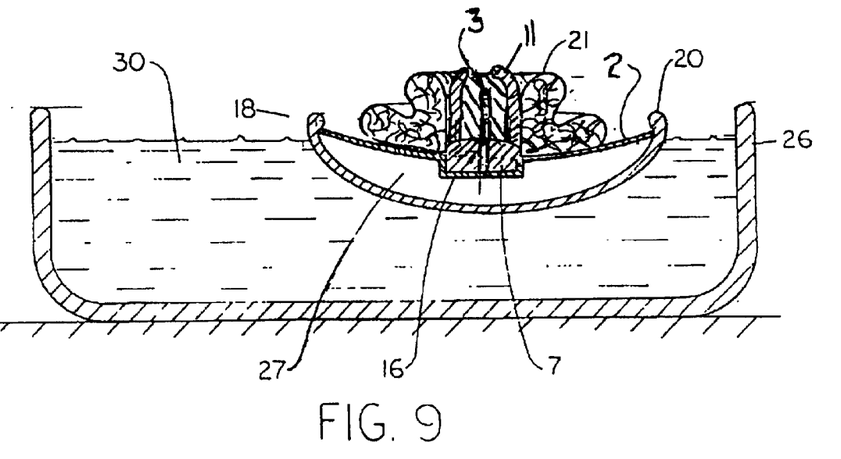
FIG. 9 is a simplified cross sectional view of a floating simmer plate dispenser, comprising a simmer plate, heat conductive element in the form of a wick holder having fins, and a solid wax refill segment.

As previously stated, the heat conductive elements, such as lobes, may be so configured as to aid in location of the solid fuel element, particularly for location of solid fuel refill elements, as shown in FIGS. 8, and 9. As shown in FIG. 8, a non-conductive container, 26, was provided, which held a simmer plate, 2, in the manner shown in FIG. 5, in juxtaposition to heat conductive lobes, 19. The lobes, as illustrated, were so configured as to act as a positioning device for a solid fuel refill element, 21, having wick 3. The lobes were situated upon a simmer plate, 2, having a recess therein (not shown) into which the refill element was inserted so as to provide close proximity of the flame, 1, on the wick, 3, to lobes 19. As illustrated, the lobes provide two recesses for positioning of refill elements, although only one refill element is shown. The heat from the flame was transmitted to the solid fuel both by radiation, and by conduction through lobes 19 and the simmer plate, 2, to rapidly melt the fuel, creating a pool of liquid fuel, 5. In this embodiment, the refill element comprised a cylindrical wax body having a fragrance included therein, similar to a votive candle, with a conventional wick. Other shapes of refill elements, such as balls, were added to the simmer plate after consumption of the original fuel element. The convex shape of the simmer plate assisted in both locating the refill elements and in assuring flow of melted fuel to the base of the wick, and the wick was retained in position by the wick clip of the candle element in the recess. Additional fuel refill elements having an active ingredient included therein were also found to be readily melted by the simmer plate dispenser shown. Refill elements in the shape of discs, cubes, balls, pucks, and various other three dimensional shapes were also used. This configuration was also found to permit easy change of active material being dispersed, by virtue of the second position for placement of a refill element, whereby refill elements having differing active ingredients could easily be alternated.

Another form of solid fuel dispenser which may employ the simmer plate and heat fin technology of this invention is the floating simmer plate dispenser. Conventional floating candles are known to tunnel very rapidly and to leave a high percentage of unburned wax, due to the cooling effect of the water upon which they float. A floating simmer plate was tested, with an insulating air gap, in conjunction with a heat fin assembly holding the wick, which insulated the wax from the body of water upon which the simmer plate floated, while heating of the wax was improved, so as to maintain a liquid wax pool for more uniform and more complete consumption of the active ingredient. As shown in FIG. 9, a container, 26, retained a body of water, 30, upon which floated a simmer plate dispenser, 18. The simmer plate dispenser comprised a bowl shaped container, 20, having a simmer plate, 2, seated therein, so as to form an insulating air gap, 27. The simmer plate had a central depression, 16, into which was placed a wax fuel element, 21, comprising a heat conductive wick holder, 7, with a heat fin 11, and a retained wick, 3. The wax fuel element, 21, fitted around the wick holder, in close proximity thereto, whereby heat was transferred efficiently from the flame, 1, at wick 3, by the heat fin assembly to the simmer plate, which thus improved melting of the wax, thereby forming a pool of liquid fuel. The outside container, 26, of the figure represents any suitable container for retention of a pool of water, or other liquid of choice, sufficient for floating a simmer plate dispenser, such as a bath tub, sink, bowl, or pool. The simmer plate container, 20, may be made of any suitable material, such as glass, ceramic, plastic, wood, etc, and may be of any desired shape, the selection of such being determined, for example, by esthetics, provided that the container be able to float safely on water while a heated fuel/active mixture is disposed therein. The solid fuel segment may be of any shape, color, configuration, or composition consistent with the present invention, designed to properly fit the simmer plate configuration, and containing the active ingredient of choice. Examples of suitable refill segments would include circular, star, clover, or flower bud or petal shapes, or any three dimensional form selected, in red, white, yellow, blue, green, or other colors, fragranced by various perfumes, or containing various other active ingredients which will volatilize at the temperature of the liquid fuel pool formed in the bowl of the simmer plate. In a conventional form of floating candle, a wax candle of low density is provided in a desired shape, configuration, and color, much in the fashion of the candle refill segments described above. In such candles, the wick is normally affixed with a conventional wick clip, and passes through the central portion of the wax body. Such candles, when floated in a body of water, suffer from short burning life, cratering, and drowning. Applicants have found that the use of a heat conductive wick holder, heat fins, and simmer plate as illustrated in FIG. 9, offers improved opportunities for aroma therapy, and other usages of active ingredients, as well as providing a floating dispenser which will burn until all of the fuel therein is consumed. The shape of such floating simmer plate dispensers may be of almost any configuration desired, with the wick holder being located centrally, or otherwise, and either single or plural. Shaping of the fuel element to any configuration is possible, as is the use of coloration for decorative purposes, along with a wide choice of actives to be included.

Similarly, when using solid fuel, such as wax, in conjunction with a heat fin or wick holder, solid fuel refill units may be shaped to fit the shape of the container, configured to fit the shape of the simmer plate, in a "lock and key" relationship. For example, the simmer plate may be a decoratively shaped container, and wax may be provided in the form of refills for the container shape selected, such as a round, square, star, clover, triangular, or other three dimensional shape, so shaped as to fit around and engage a complimentarily shaped lobe or heat fin, for example.

One embodiment of the present invention includes simmer plate dispensers suitable for use outdoors as space repellents for insects. It is known that existing outdoor candles are not exceptionally efficient at dispersing actives into the surrounding atmosphere, due to the relatively low temperatures attained in the wax pool of the conventional candle dispenser. Further, those actives which are carried to the point of burning at the flame seldom impart a significant effect upon the surrounding atmosphere, due to decomposition at flame temperatures rather than release to the atmosphere. Some of the most efficacious actives currently available have evaporation temperatures higher than the temperatures of the wax pool formed in a conventional candle. When such an active is added to wax, it is usually consumed in the flame, and is thus not effectively dispersed to the atmosphere. By the use of a conductive simmer plate and a heat conductive fin, as set forth in the present invention, Applicants have enabled at least a portion of the wax pool to reach temperatures significantly above the normal melting point of the solid fuel, thus allowing the active to reach a temperature which is high enough to cause its evaporation before it was consumed in the flame. Use of a heat fin assembly such as shown in FIG. 3e, which may position a heat conductive element directly in the flame at its highest temperature location, permits attaining temperatures previously unattainable, sufficient to melt and evaporate waxes containing most active ingredients presently available for such use as insect repellents or insecticide, including such high volatilization temperature materials as Pynamine Forte. By using such dispensing devices, the active materials in the wax are heated to above their evaporation temperatures, thus providing the maximum utilization of the active ingredient. Such dispensing devices preferably comprise highly conductive simmer plates, mounted in non-conductive containers, and utilize refill units comprising a solid fuel with the desired active ingredient included therein. In such a manner, the consumer may be provided with a simmer plate dispenser suitable for a multitude of uses, such as fragrancing, insect control, and mood enhancement, merely by choice of the fuel refill element employed.

The use of a simmer plate with additional heat conductive elements offers a number of distinct advantages. First, it permits a larger pool of liquid fuel, due to improved heat conduction into the fuel, which results in more rapid formation of the pool. This in turn allows better regulation of the size and temperature of the liquified wax pool to allow more efficient use of fuel and more rapid evaporation of the active ingredients present. In fact, simmer plates permit more frequent fragrance changes, with little or no cleaning, and evaporation of actives which would not be possible if incorporated into existing oil/wax products. The use of lobes in the simmer plate in conjunction with heat fins in the fuel element also reduces or eliminates retention of solidified excess fuel when the dispenser is allowed to burn itself out, and permits more complete and uniform burning of fuel elements which are other than round, i.e. square, oval, triangular, or in the shape of a flower or decorative object, etc. Further, the simmer plate technology results in devices which may be self extinguishing, and improvements in or elimination of typical burning problems encountered with candles, such as tunneling, drowning, collapsing, cratering, and wick drift. Dispensers utilizing the simmer plate technology of the present invention are also more forgiving of formulation or process variances.

EXAMPLES

A number of tea lights were prepared to test the efficiency of the invention relative to heat distribution and melting of the wax fuel. In the following Examples, all candles comprised the same wax, and were of the same dimension, with identical consumable wicks. Examples comprised tea lights with conventional wick clips in a conventional aluminum container, tea lights with conventional wick clips but no container, and tea lights with a finned wick clip and heat plate as set forth in the present invention. Temperatures of the wax pool were measured at distances of 10 and 20 mm from the wick, using infrared temperature measuring methods.

TABLE 1

Time vs. Temperature (° F.) 10 mm from wick

| Minutes | Regular clip Regular container | Regular clip No container | Finned Clip Heat Plate |
| --- | --- | --- | --- |
| 10 | 148 | 147 | 115 |
| 15 | 147 | 142 | 121 |
| 20 | 144 | 137 | 128 |
| 25 | 142 | 139 | 136 |
| 30 | 141 | 137 | 144 |
| 40 | 144 | 139 | 128 |
| 50 | 146 | 138 | 146 |
| 60 | 154 | 141 | 177 |
| 70 | 168 | 138 | 203 |
| 80 | 170 | 143 | 208 |
| 90 | 172 | 142 | 200 |
| 120 | 171 | 143 | 172 |
| 150 | 158 | | |

In this experiment, the regular clip/regular container tea light burned out after 152 minutes, the regular clip/no container tea light burned out after 123 minutes, and the finned clip tea light burned out after 125 minutes. It may be seen that the tea light employing the finned clip achieved a much higher temperature in the wax pool than either of the other tea lights, and the temperature of said pool of liquid fuel exceeds a temperature of about 180° F. at a point about 10 mm from said wick.

TABLE 2

Time vs. Temperature (° F.) 20 mm from wick

| Minutes | Regular clip Regular container | Regular clip No container | Finned Clip Heat Plate |
| --- | --- | --- | --- |
| 10 | 78 | 80 | 79 |
| 15 | 80 | 138 | 83 |
| 20 | 80 | 118 | 87 |
| 25 | 82 | 107 | 89 |
| 30 | 85 | 113 | 91 |
| 40 | 88 | 119 | 93 |
| 50 | 89 | 128 | 130 |
| 60 | 93 | 127 | 165 |
| 70 | 97 | 136 | 172 |
| 80 | 99 | 139 | 174 |
| 90 | 102 | 137 | 167 |
| 120 | 108 | 119 | 135 |
| 150 | 117 | | |

In this experiment, the regular clip/regular container tea light burned out after 152 minutes, the regular clip/no container tea light burned out after 123 minutes, and the finned clip tea light burned out after 125 minutes. It may be seen that the tea light employing the finned clip achieved a much higher temperature in the wax pool than either of the other tea lights, exceeding a temperature of about 160° F. at a point about 20 mm from said wick. Such high temperatures are responsible for improved distribution of active materials from the wax pool by means of more efficient evaporation.

While the present invention has been described with respect to what are at present considered to be the preferred embodiments, it is to be understood that the invention is not to be limited to the disclosed embodiments. To the contrary, the invention is intended to cover various modifications and equivalent arrangements within the spirit and scope of the appended claims. The scope of the following claims is to be accorded the broadest interpretation so as to encompass all such modifications and equivalent formulations and functions.

INDUSTRIAL APPLICABILITY

The simmer plate and heat conductive element dispensers of the present invention can be used in connection with a large variety of solid fuels comprising active ingredients, such as for aroma therapy, and dispersal of actives such as herbals, fragrances, disinfectants, insecticides, and insect repellents. The conductive materials of which the simmer plate and heat fins may be constructed are commonly available, as are the various active materials suitable for inclusion in the fuel elements, and the various configurations are readily produced.

What is claimed is:

1. A simmer plate dispenser for active materials, said dispenser comprising, in combination, a meltable solid fuel comprising a volatile active material, a consumable wick, a heat conductive base upon which said fuel rests having heat conductive elements comprising at least one lobe in said base by which heat is conducted to said base from a flame upon said wick, whereby a pool of heated liquid fuel is created from which said active material volatilizes, wherein said heat conductive base is configured so as to cause the flow of said heated liquid fuel to said wick for combustion, said base and said heat conductive elements are configured so as to cooperatively engage said solid fuel, and said active material is selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof.

2. The dispenser of claim 1, wherein said fuel is selected from the group consisting of gels and solid waxes.

3. The dispenser of claim 1, wherein said volatile active is selected from the group consisting of fragrances, air fresheners, insect repellants, herbal substances, mood enhancers, and aroma therapy compositions.

4. A simmer plate dispenser for dispersing an active ingredient selected from the group consisting of fragrances, air fresheners, deodorizers, odor eliminators, odor counteractants, insecticides, insect repellants, herbal substances, medicinal substances, disinfectants, sanitizers, mood enhancers, aroma therapy compositions, and mixtures thereof, said dispenser comprising a replaceable fuel containing said ingredient and a wick, and a dispensing device comprising a heat conductive simmer plate, and a heat conductive element to collect heat from a flame at said wick and conduct said heat to said simmer plate to thereby melt said fuel containing said active ingredient and form a pool of liquid fuel on the surface of said simmer plate, wherein said dispensing device is configured to position and engage said fuel on said simmer plate for rapid melting, said simmer plate is shaped so as to cause said pool of liquid fuel to flow to said wick, said active ingredient is selected so as to evaporate from said pool of liquid fuel, and the temperature of said pool of liquid fuel exceeds a temperature of about 180° F. at a point about 10 mm from said wick, and about 160° F. at a point about 20 mm from said wick.

5. A simmer plate dispenser as set forth in claim 4, wherein said heat conductive element is selected from the group consisting of lobes, fins, wick holders, and combinations thereof.

6. The dispenser of claim 5, wherein said heat conductive element is a lobe, and said active ingredient is selected from the group consisting of fragrances, air fresheners, insect repellants, herbal substances, mood enhancers, and aroma therapy compositions.

7. The dispenser of claim 5, wherein said heat conductive element is a wick holder with fins, and said active ingredient is selected from the group consisting of fragrances, air fresheners, insect repellants, herbal substances, mood enhancers, and aroma therapy compositions.

8. A dispensing device for dispersing a volatile active material, said device comprising a heat conductive container for a replaceable fuel element comprising a combustible wick and said volatile active material, said container comprising a heat conductive lobe whereby heat is conducted to said fuel element and said container, said container and lobe configured so as to engage and melt said solid fuel element and to cause the flow of melted fuel to said wick.

9. A dispensing device as set forth in claim 8, wherein said container comprises a concave simmer plate constructed of a heat conductive material selected from the group consisting of brass, aluminum, steel, copper, stainless steel, silver, tin, bronze, zinc, iron, clad materials, heat conductive polymers, ceramics, glass, and combinations thereof.

* * * * *